United States Patent
Meyer Rojas et al.

(10) Patent No.: US 11,739,327 B2
(45) Date of Patent: Aug. 29, 2023

(54) POSITIONAL DELIVERY AND ENCODING BY OLIGONUCLEOTIDES OF BIOLOGICAL CELLS FOR SINGLE CELL SEQUENCING (POS SEQ)

(71) Applicant: International Business Machines Corporation, Armonk, NY (US)

(72) Inventors: Pablo Meyer Rojas, Brooklyn, NY (US); Gustavo Alejandro Stolovitzky, Riverdale, NY (US)

(73) Assignee: International Business Machines Corporation, Armonk, NY (US)

( * ) Notice: Subject to any disclaimer, the term of this patent is extended or adjusted under 35 U.S.C. 154(b) by 567 days.

(21) Appl. No.: 16/846,297

(22) Filed: Apr. 11, 2020

(65) Prior Publication Data

US 2021/0317449 A1    Oct. 14, 2021

(51) Int. Cl.
| | | |
|---|---|---|
| C12N 15/113 | (2010.01) | |
| C12N 15/10 | (2006.01) | |
| C12Q 1/6869 | (2018.01) | |
| C40B 20/04 | (2006.01) | |

(52) U.S. Cl.
CPC ........ *C12N 15/113* (2013.01); *C12N 15/1096* (2013.01); *C12Q 1/6869* (2013.01); *C40B 20/04* (2013.01)

(58) Field of Classification Search
CPC ............ C12Q 1/6869; C12Q 2563/179; C12N 15/113; C12N 15/1096; C40B 20/04
See application file for complete search history.

(56) References Cited

U.S. PATENT DOCUMENTS

| | | |
|---|---|---|
| 2016/0274097 A1 | 9/2016 | Megede |
| 2017/0233722 A1 | 8/2017 | Seelig et al. |
| 2018/0127744 A1 | 5/2018 | Hu et al. |
| 2018/0305681 A1 | 10/2018 | Jovanovich et al. |
| 2020/0157528 A1 | 5/2020 | Vogel et al. |
| 2022/0229044 A1* | 7/2022 | Feldman ............. C12N 15/102 |

FOREIGN PATENT DOCUMENTS

| | | |
|---|---|---|
| WO | WO2018075436 A1 | 4/2018 |
| WO | WO2019051335 A1 | 3/2019 |
| WO | WO2019126209 A1 | 6/2019 |

OTHER PUBLICATIONS

Mell et al., "The NIST Definition of Cloud Computing," NIST Special Publication 800-145, Sep. 2011 (7 pages).
Juncker et al., "Multipurpose microfluidic probe," Nature Materials, Advanced Online Publication (Jul. 2005) (8 total pages).
Zhu et al., "Reverse Transcriptase Template Switching: A SMARTTM Approach for Full-Length cDNA Library Construction," BioTechniques 30:892-897 (Apr. 2001).
Macosko et al., "Highly Parallel Genome-wide Expression Profiling of Individual Cells Using Nanoliter Droplets," Cell 161, 1202-1214 (May 2015).
Gagat et al., "Cell-penetrating peptides and their utility in genome function modifications (Review)," International Journal of Molecular Medicine 40: 1615-1623 (Oct. 2017).
Rodriques et al., "Slide-seq: A scalable technology for measuring genome-wide expression at high spatial resolution," Science 363, 1463-1467 (Mar. 2019).
Lovatt et al., "Transcriptome in vivo analysis (TIVA) of spatially defined single cells in live tissue," Nature Methods, vol. 11, No. 2 (Feb. 2014) (10 pages).
Hanahan et al., "Hallmarks of Cancer: The Next Generation," Cell 144, pp. 646-674 (Mar. 2011).
Tanese et al., "Domain structure of the Moloney murine leukemia virus reverse transcriptase: Mutational analysis and separate expression of the DNA polymerase and RNase H activities," Proc. Natl. Acad. Sci., vol. 85, pp. 1777-1781 (Mar. 1988).
Lovchik et al., "Micro-immunohistochemistry using a microfluidic probe," Lab on a Chip (Jan. 2012) (4 pages).
Huber et al., "Micro fluorescence in situ hybridization (µFISH) for spatially multiplexed analysis of a cell monolayer," Biomed Microdevices 18:40 (Apr. 2016).
Kashyap et al., "Selective local lysis and sampling of live cells for nucleic acid analysis using a microfluidic probe," Scientific Reports, 6:29579 (Jul. 2016) (10 pages).

* cited by examiner

*Primary Examiner* — David C Thomas
(74) *Attorney, Agent, or Firm* — Kristofer Haggerty; Michael J. Chang, LLC

(57) ABSTRACT

Techniques for positional delivery and position encoding by oligonucleotides of biological cells for single cell RNA sequencing are provided. In one aspect, a method of positional delivery and encoding of cells in a biological sample includes: encoding the cells in the biological sample for single cell sequencing by delivering molecular probes inside the cells that encode a position of the cells in the biological sample. A system for positional delivery and encoding of cells in a biological sample is also provided.

19 Claims, 9 Drawing Sheets

POSITIONAL DELIVERY AND ENCODING BY OLIGONUCLEOTIDES OF BIOLOGICAL CELLS FOR SINGLE CELL SEQUENCING (POS SEQ)

FIELD OF THE INVENTION

The present invention relates to single cell sequencing, and more particularly, to techniques for positional delivery and position encoding by oligonucleotides of biological cells for single cell ribonucleic acid (RNA) sequencing, i.e., positional sequencing (POS SEQ).

BACKGROUND OF THE INVENTION

The successful functioning of multi-cellular organisms relies on the coordinated functions of a multitude of molecular constituents from individual cells and the interactions among functionally distinct cells. Further, these molecular constituents are constantly changing such as in response to cell-to-cell interactions which oftentimes result from local physical cell-to-cell contact and/or from short length-scale paracrine cell-to-cell communications. Thus, the state of a biological system is often defined by the relative position of the cells in the system and the highly dimensional molecular composition of each of those cells.

For example, with diseases such as cancer, specific tumor cell subpopulations can co-opt adjacent normal cells to support tumor progression. Thus, the relevance of cell positioning has motivated the development of therapeutic agents that target the co-opted cells, such as platelet-derived growth factor receptor ("PDGFR") inhibitors to target PDGFR+ pericytes, and small molecule inhibitors or neutralizing antibodies of colony-stimulating factor 1 ("CSF1") receptors to target macrophages.

Typically, spatial and molecular measurements are made using image-based analysis where molecular and positional information is obtained by taking microscopy images of samples treated with either enzymatically- or fluorescently-labeled antibodies that bind specifically to the molecular target of interest. When the images are digital, the sensor pixel position reflects the spatial relationship of the cells, while the sensor pixel signal intensity reflects the local density of the labeled antibodies molecular target of interest.

Other techniques employed for concomitant spatial and molecular measurements involve first recording the positioning of the individual cells that are then measured. It is however impractical to implement such a technique with potentially millions of distinct cells that need to be stored and processed separately for molecular profiling.

Thus, improved techniques for concomitant spatial and molecular measurements of biological cells would be desirable.

SUMMARY OF THE INVENTION

The present invention provides techniques for positional delivery and position encoding by oligonucleotides of biological cells for single cell ribonucleic acid (RNA) sequencing (POS SEQ). In one aspect of the invention, a method of positional delivery and encoding of cells in a biological sample is provided. The method includes: encoding the cells in the biological sample for single cell sequencing by delivering molecular probes inside the cells that encode a position of the cells in the biological sample.

In another aspect of the invention, another method of positional delivery and encoding of cells in a biological sample is provided. The method includes: constructing a cDNA library of molecular probes that encode a position of cells in a biological sample; linking the molecular probes to a vessel; delivering the vessel with the molecular probes to specific locations of the biological sample where the vessel delivers the molecular probes inside the cells at the specific locations; extracting the cells containing the molecular probes from the sample; and performing single cell sequencing of the extracted cells.

In yet another aspect of the invention, a system for positional delivery and encoding of cells in a biological sample is provided. The system includes: a processor device, connected to a memory, that is implemented to: analyze data from single cell sequencing of cells along with molecular probes, that have been delivered inside the cells, which uniquely encode a position of the cells in a biological sample.

A more complete understanding of the present invention, as well as further features and advantages of the present invention, will be obtained by reference to the following detailed description and drawings.

DETAILED DESCRIPTION OF PREFERRED EMBODIMENTS

Provided herein are techniques for concomitant positional and molecular measuring of cells using a molecular probe having a unique oligonucleotide sequence that encodes a positioning of the cells within a biological sample such as a cell culture (e.g., a cell culture including living eukaryotic and/or prokaryotic cells) and/or a tissue sample (e.g., a biopsy, formalin-fixed paraffin-embedded ("FFPE") and/or frozen tissue containing living cells). Thus, when the cells are later dissociated from the biological sample and sequenced, the cells will take with them the positional information encoded in the molecular probe. Advantageously, the molecular probe encodes the position at which each of the cells being sequenced is located within the biological sample.

As will be described in detail below, the molecular probe is first linked to a vessel such as a retrovirus, disulfide-linked cell-penetrating peptide (CPP) and/or bead micro-particle. A liquid cargo delivery device such as a microfluidic probe (MFP) is then used to deliver the molecular probe/vessel to specific locations of the biological sample. See, for example, Juncker et al., "Multipurpose microfluidic probe," Nature Materials, Advanced Online Publication (July 2005) (8 total pages), the contents of which are incorporated by reference as if fully set forth herein. By way of the vessel, the molecular probes with unique nucleotide sequences are delivered inside the cells at those specific locations of the biological sample. As highlighted above, these oligonucleotide sequences are in effect a label of the position of a given cell in the biological sample. Thus, for each location (x,y) of a biological sample that the liquid cargo delivery device visits, a unique oligonucleotide sequence is delivered inside the cells at that location in the biological sample.

Figure 1:
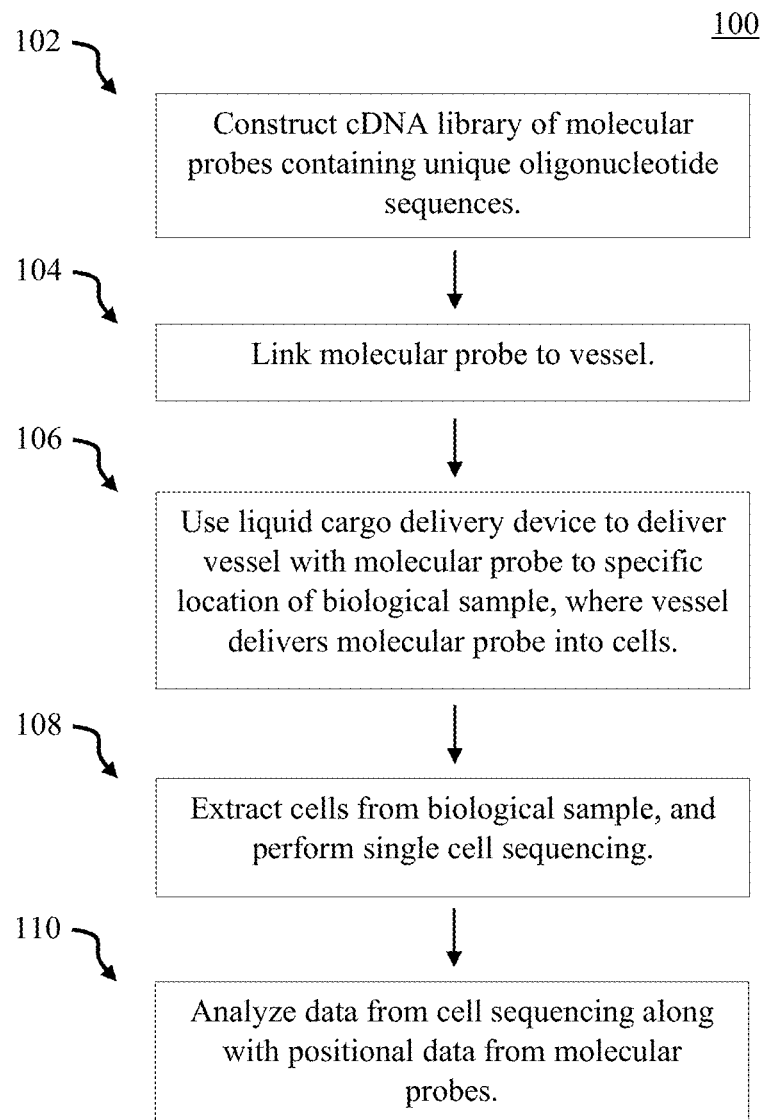
FIG. 1 is a diagram illustrating an exemplary methodology of positional delivery and encoding of cells in a biological sample for single cell sequencing according to an embodiment of the present invention.

An overview of the present techniques for positional delivery and encoding of cells in a biological sample for single cell sequencing is now provided by way of reference to methodology 100 of FIG. 1. In step 102, a complementary deoxyribonucleic acid (cDNA) library of molecular probes containing unique oligonucleotide sequences is constructed. As will be described in detail below, according to an exemplary embodiment, the library construction leverages the template-switching activity of Moloney murine leukemia virus reverse transcriptase ("MMLV RT"). For a general description of MMLV RT for library construction see, for example, Zhu et al., "Reverse Transcriptase Template Switching: A SMART™ Approach for Full-Length cDNA Library Construction," BioTechniques 30:892-897 (April 2001) (hereinafter "Zhu"), the contents of which are incorporated by reference as if fully set forth herein.

In step 104, the molecular probes with unique oligonucleotide sequences are then linked to a particular vessel such as a retrovirus, coupled to a disulfide-linked cell-penetrating peptide (CPP) or a bead micro-particle. This vessel will enable the molecular probes to be delivered inside the cells of a biological sample. By delivering the molecular probes into the cells, the cells can be uniquely identified—even when disassociated from the biological sample—due to the unique oligonucleotide sequences carried by the molecular probes.

In step 106, the vessels with the molecular probes are delivered to specific locations of the biological sample (e.g., a living cell culture and/or tissue sample with living cells), where the vessels deliver the molecular probes inside the cells at those specific locations. According to an exemplary embodiment, this location-specific delivery is accomplished using a liquid cargo delivery device such a microfluidic probe or MFP. A microfluidic probe is a non-contact, scanning platform that can hydrodynamically localize as little as 100 picoliters of a liquid cargo with micrometer precision. For instance, the molecular probes can be dispersed in a processing solution (e.g., an aqueous solution) that is then delivered via the liquid cargo delivery device to specific locations of the biological sample. The molecular probes delivered to a given specific location of the biological sample contain a unique oligonucleotide sequence that is associated with that given specific location. Thus, as provided above, when the cells are later disassociated from the biological sample for sequencing, the oligonucleotide sequence encodes the original position of the cells in the sample (i.e., positional encoding).

Once the molecular probes are delivered to a given specific location of the biological sample, the vessels deliver the molecular probes inside the cells at those specific locations. According to an exemplary embodiment, the cells take in the vessels with the molecular probes through an active transfection/transduction process using living cell machinery. Thus, the present techniques are preferably performed with a living biological system. For instance, the biological sample preferably contains living cells, whether as a living cell culture or as a tissue sample containing living cells. The living cells permit transfection/transduction to occur. Following the present positional encoding process, the cells/tissue can be fixed if so desired.

In step 108, single cell sequencing is performed on the cells extracted from the biological sample. Even though the cells are disassociated from the biological sample for sequencing, the cells now contain the molecular probe with oligonucleotide sequence encoding the position of the cells in the biological sample. Thus, this positional data can be retained through the sequencing process.

For instance, in step 110 the data from the single cell sequencing is stored and analyzed (e.g., in silico) along with the data from the molecular probes which uniquely encodes the positions of the cells in the biological sample. An exemplary apparatus for storing and analyzing this data is provided in FIG. 9, described below. Being able to analyze transcriptomic data (i.e., RNA transcripts produced by a genome) from the cells along with the position of those cells in the biological sample is extremely beneficial. For instance, as highlighted above, the state of a biological system is often defined by the relative position of the cells in the system and the highly dimensional molecular composition of each of those cells. Take, for example, the development of therapeutic agents for cancer treatment that leverage cell positioning to target specific tumor cell subpopulations. See above.

Figure 2:
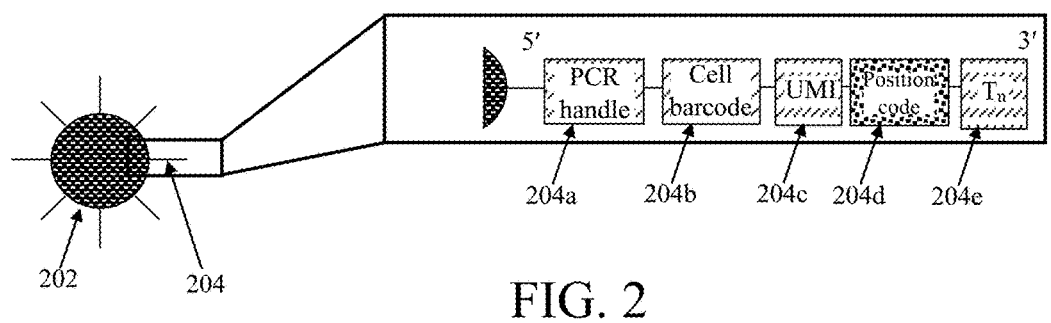
FIG. 2 is a diagram illustrating an exemplary barcoded deoxyribonucleic acid (DNA) oligonucleotide primer molecule according to an embodiment of the present invention.

As described in conjunction with the description of step 102 of methodology 100 above, the process begins with the construction of a cDNA library of molecular probes containing unique oligonucleotide sequences for positional encoding. As shown in FIG. 2, the cDNA library construction begins with many barcoded DNA oligonucleotide primer molecules 204 conjugated to a microparticle 202 (e.g., a bead) such as a glass bead. The techniques for preparing distinctly barcoded oligonucleotide primers are described generally in Macosko et al., "Highly Parallel Genome-wide Expression Profiling of Individual Cells Using Nanoliter Droplets," Cell 161, 1202-1214 (May 2015), the contents of which are incorporated by reference as if fully set forth herein.

As shown in FIG. 2, beginning from its 5' end, each DNA oligonucleotide primer molecule 204 contains a universal polymerase chain reaction (PCR) handle 204a, a cell barcode 204b, a unique molecular identifier (UMI) 204c, a position code 204d, and a poly T sequence 204e (i.e., Tn—a sequence of n thymine repeats). PCR handle 204a enables PCR amplification. For example, according to an exemplary embodiment, PCR handle 204a is a DNA oligonucleotide sequence for PCR primers in the amplification step (see, e.g., FIG. 4—described below).

Cell barcode 204b is a DNA oligonucleotide sequence that is unique to bead 202/cell into which the molecular probe is delivered. UMI 204c is a DNA oligonucleotide sequence that is unique to this particular DNA oligonucleotide primer molecule 204. For instance, the DNA oligonucleotide primer molecules attached to the same bead 202 can share the same cell barcode, but different UMIs. In other words, the UMIs of each DNA oligonucleotide primer molecules has a different, unique oligonucleotide sequence. By way of example only, the UMIs can be used for normalizing gene counts during computational data processing. For example, the UMIs can be used to identify PCR duplicates during the single cell sequencing (see below).

The position code 204d provides the (location-specific) oligonucleotide sequence for positional encoding. Namely, as described above, the position code 204d uses a unique oligonucleotide sequence to encode the location (x,y) of cells in a biological sample into which the present molecular probes will be delivered. A length of the position code 204d can depend on the total number of locations (x,y) to be encoded. For example, according to an exemplary embodiment, the length of the position code 204d is determined as follows, $$L \geq \log 4(N), \quad (1)$$

wherein L represents the length of the position code 204d (i.e., the number of nucleotides that make up the position code 204d), and wherein N represents the total number of locations (x,y) to be encoded. As will be described below, the library and/or library construction (such as the generation of the location-specific oligonucleotide sequence for positional encoding) can optionally be provided as a service in a cloud environment.

Figure 3:
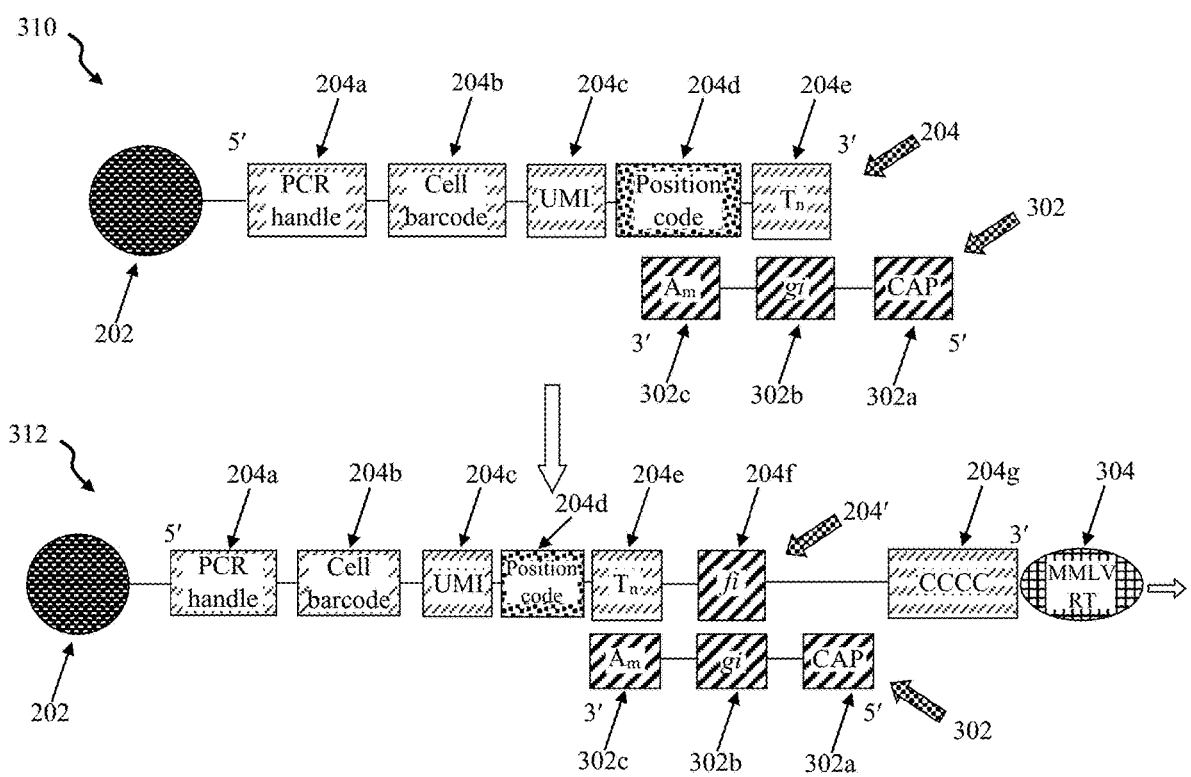
FIG. 3 is a diagram illustrating an exemplary methodology for constructing a cDNA library using Moloney murine leukemia virus reverse transcriptase (MMLV RT) technology according to an embodiment of the present invention.

According to an exemplary embodiment, the cDNA library is constructed using MMLV RT. See, for example, FIG. 3 where an endogenous messenger RNA (mRNA) template 302 hybridizes with DNA oligonucleotide 204, and MMLV RT 304 synthesizes a DNA complement (cDNA) to the mRNA template 302, and then appends a poly cytosine (C) sequence to the newly synthesized cDNA sequence. For instance, as shown in step 310, in its simplest form mRNA template 302 of the $i^{th}$ gene includes a generic 5' CAP 302a, a gene-specific coding region $g_i$ 302b, and a poly A tail 302c (i.e., a sequence of m adenine (A) repeats).

As shown in step 312, the mRNA template 302 hybridizes with the 3' poly T sequence 204e of DNA oligonucleotide 204, and the MMLV RT 304 synthesizes a DNA complement (see for example gene-specific coding region $f_i$ 204f) to the mRNA template 302. This new cDNA sequence is now given reference numeral 204'. MMLV RT 304 then appends cDNA sequence 204' with poly C sequence 204g.

Figure 4:
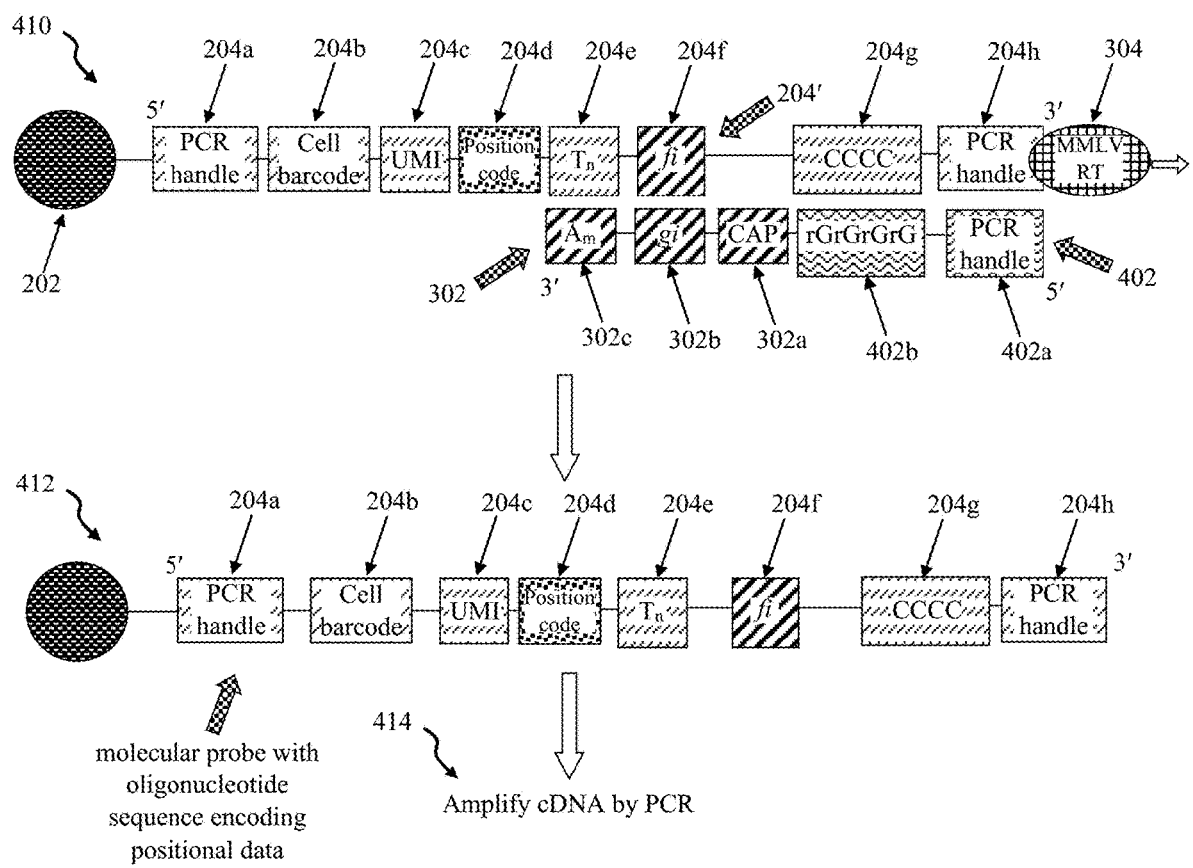
FIG. 4 is a diagram illustrating an exemplary methodology for a 'template switch' by the MMLV RT using a template switch oligonucleotide (TSO) sequence according to an embodiment of the present invention.

According to an exemplary embodiment, a template switch is performed where a template switch oligonucleotide (TSO) sequence 402 is hybridized with the cDNA sequence 204', after which the MMLV RT 304 performs the 'template switch' in which MMLV RT 304 uses the TSO sequence 402 as a template for replication. See FIG. 4. As shown in FIG. 4, TSO sequence 402 includes two groups, an oligonucleotide code 402a that one wants to append to the mRNA template 302, and a poly ribosomal Guanine (rG) repeat sequence 402b. According to an exemplary embodiment, the oligonucleotide code 402a is a PCR handle. As provided above, a PCR handle enables PCR amplification.

As shown in step 410, the poly rG sequence 402b of TSO 402 hybridizes with the poly C sequence 204g (that was appended to the cDNA sequence 204' by MMLV RT 304—see above). Doing so enables the MMLV RT 304 to then use TSO 402 as a template for replication. For instance, as shown in step 410 MMLV RT 304 appends a PCR handle 204h to the poly C sequence 204g at the 3' end of cDNA sequence 204'.

As shown in step 412, the cDNA sequence 204' is then separated from the mRNA template 302/TSO 402. By way of example only, the cDNA sequence 204' can be separated from the mRNA template 302/TSO 402 by ribonuclease H activity of the MMLV RT technology and/or through the use of RNA degradation by sodium hydroxide (NaOH) and heat. The result is a molecular probe with a unique oligonucleotide sequence (i.e., position code 204d) that encodes positional data. For instance, as highlighted above, each molecular probe is location-specific, meaning that it contains an oligonucleotide sequence position code 204d that is unique to a specific location of a biological sample. By way of the present techniques, the molecular probes are then delivered inside the cells at specific locations of the biological sample corresponding to the oligonucleotide sequence position code 204d each of molecular probe carries. As shown in step 414, the cDNA sequence 204'/molecular probes can be amplified by PCR.

Figure 5:
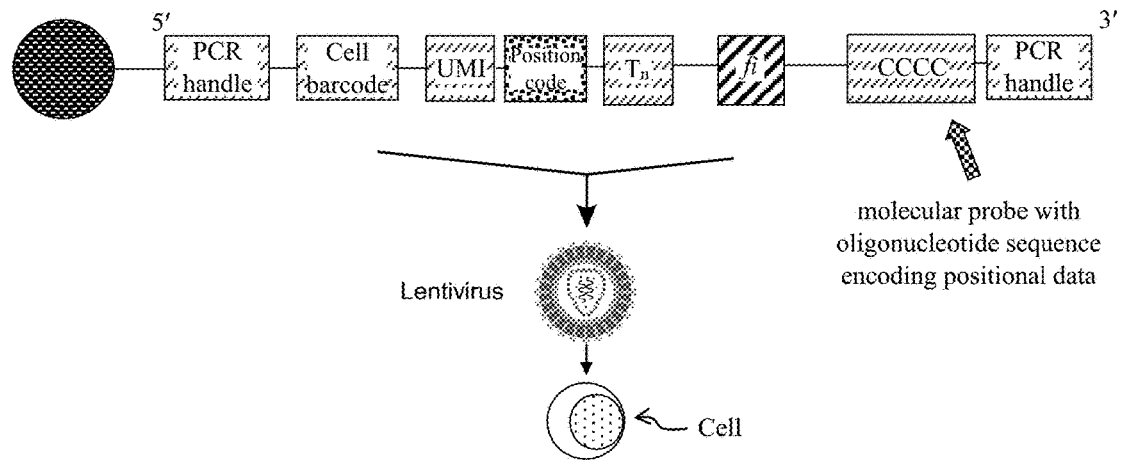
FIG. 5 is a diagram illustrating use of a lentiviruses as the vessel for delivering a location-specific molecular probe inside the cells of a biological sample according to an embodiment of the present invention.

As described in conjunction with the description of step 104 of methodology 100 above, the molecular probes with unique oligonucleotide sequences are then linked to a vessel such as a retrovirus, coupled to disulfide-linked cell-penetrating peptide (CPP) or bead micro-particle which will permit transfer of molecular probes into the cells at specific locations of the biological sample. For live cells, retroviruses such as lentiviruses like the MMLV can be employed as the vessel. See FIG. 5. Lentiviruses such as MMLV are advantageous as gene delivery vehicles because they are able to stably integrate into the genome of cells. Further, among retroviruses, lentiviruses have the distinguishing property of being able to insert genetic material into both dividing and non-dividing cells. The process for modifying retroviruses such as lentiviruses for use as vectors for gene delivery into cells is well known to those of ordinary skill in the art.

Figure 6:
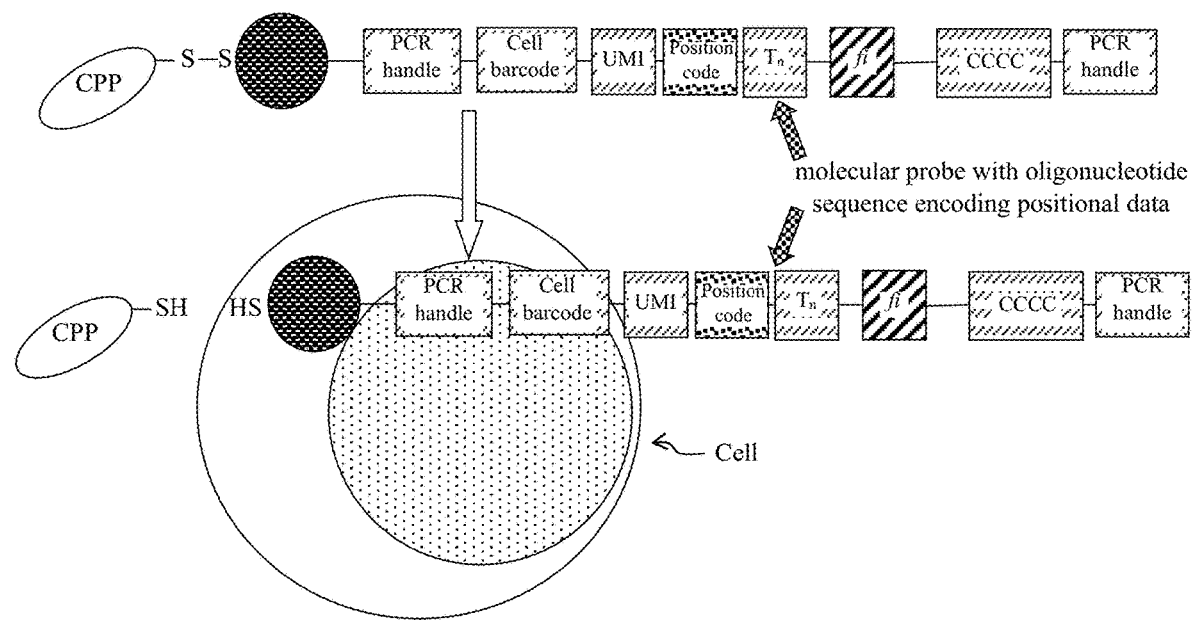
FIG. 6 is a diagram illustrating use of a disulfide-linked cell-penetrating peptide (CPP) as the vessel for delivering a location-specific molecular probe inside the cells of a biological sample according to an embodiment of the present invention.

A disulfide-linked cell-penetrating peptide (CPP) or activatable cell-penetrating peptide (ACCP) is also a suitable vessel for transferring the molecular probes into the cells of the biological sample when the sample is live cells or tissue containing live cells. See FIG. 6. CPP are biocarriers that are able to penetrate biological membranes and thus translocate into cells, thereby permitting the cells to internalize different cargo molecules. According to an exemplary embodiment, the CPPs are short polycations attached via protease-cleavable linkers to neutralizing polyanions. Thus, as shown in FIG. 6, the disulfide-linked CPP-to-oligonucleotides complexes are non-permanent in the reducing environment within the cells. As such, once the CPP biocarriers deliver the molecular probes into the individual cells of the biological sample, the disulfide bond between the CPP biocarrier molecule and the molecular probe can be cleaved. For a general description of CPP molecules as biocarriers see, for example, Gagat et al., "Cell-penetrating peptides and their utility in genome function modifications (Review)," International Journal of Molecular Medicine 40: 1615-1623 (October 2017), the contents of which are incorporated by reference as if fully set forth herein.

Figure 7:
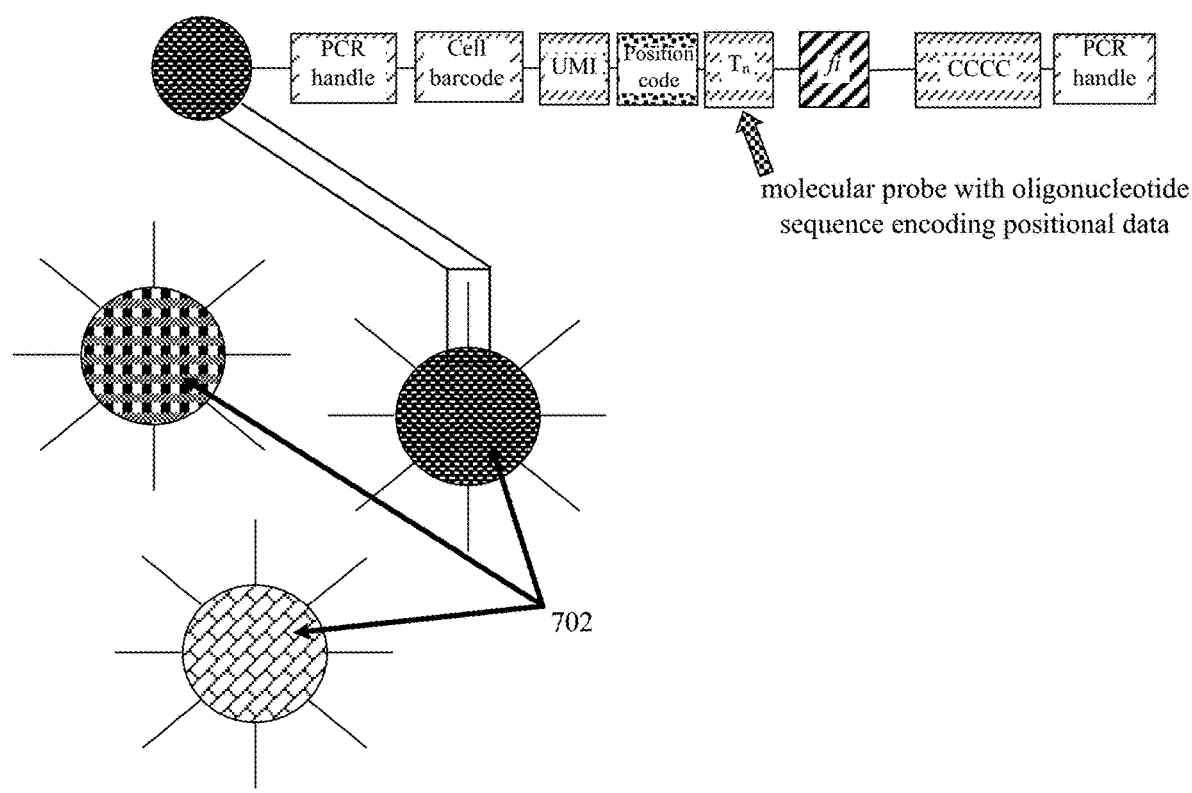
FIG. 7 is a diagram illustrating use of bead micro-particles as the vessel for delivering a location-specific molecular probe inside the cells of a biological sample according to an embodiment of the present invention.

For tissue with living cells, bead micro-particles 702 are also a suitable vessel for transferring the molecular probes into the cells of the biological sample. See FIG. 7. Beads micro-particles 702 are able to permeate the biological membranes of cells by a process called bead transfection. For instance, micro-particle beads such as glass beads can first be incubated in a solution containing the molecular probes. The micro-particle beads now conjugated with molecular probes can then be introduced into the cells using a process such as electroporation. According to an exemplary embodiment, the bead micro-particles 702 are the same as bead 202 described above (see FIG. 2). Other vessel delivery mechanisms (such as a retrovirus, coupled to a disulfide-linked CPP, etc.) are needed because some mechanisms are better than others, depending on if they are being used for tissues or cells.

Figure 8:
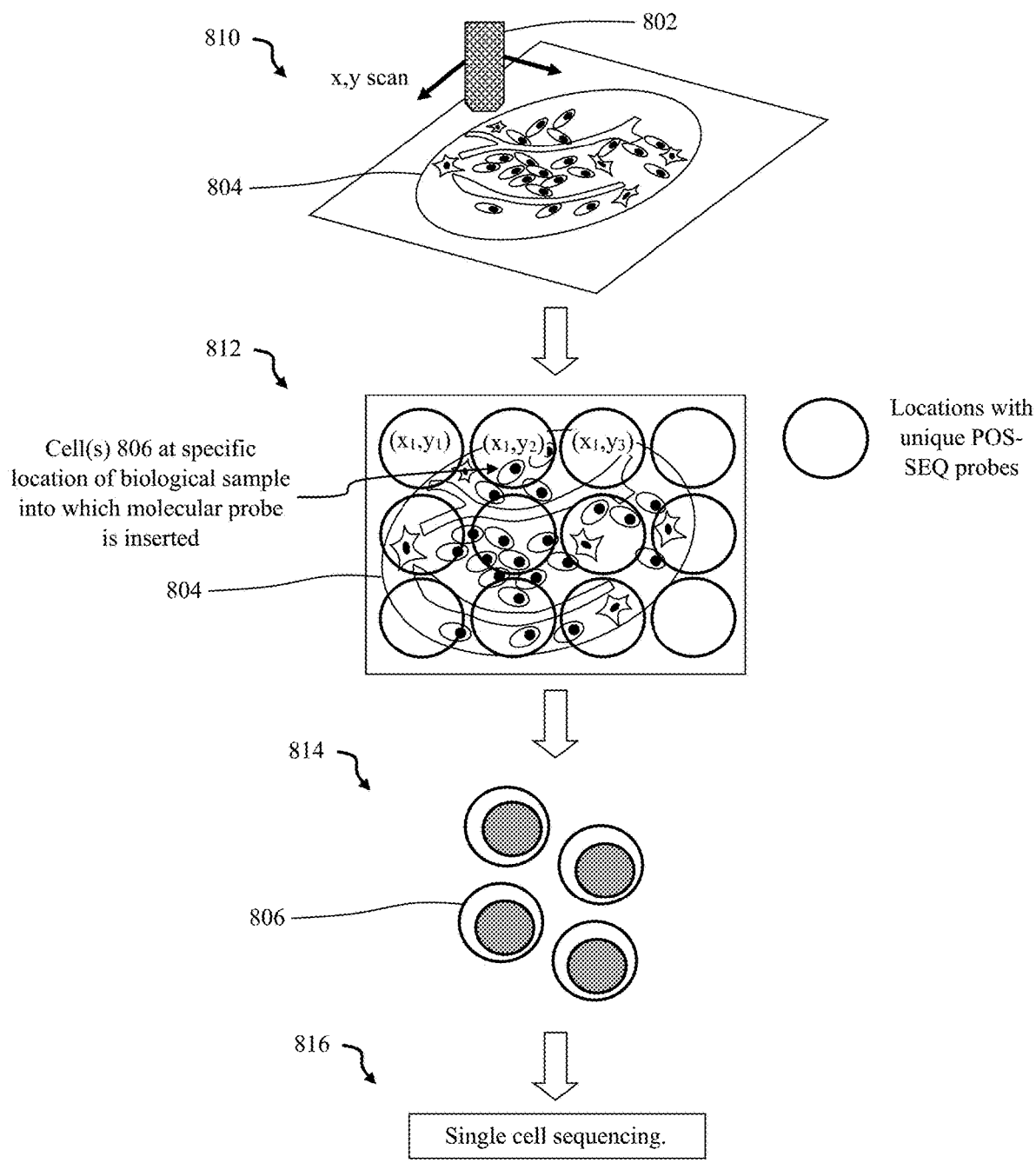
FIG. 8 is a diagram illustrating an exemplary methodology for using a liquid cargo delivery device to deliver the vessels with unique molecular probes to specific locations of the biological sample, where the vessel delivers the location-specific molecular probes inside the cells at those locations for single cell sequencing according to an embodiment of the present invention.

As described in conjunction with the description of step 106 of methodology 100 above, a liquid cargo delivery device such as a microfluidic probe is employed to deliver the vessels with unique molecular probes to specific locations of the biological sample, where the vessel delivers the location-specific molecular probes inside the cells at those locations. See, for example, FIG. 8. In step 810, a liquid cargo delivery device 802 (such as a microfluidic probe) scans the surface of a biological sample 804 and deposits the vessels with unique molecular probes at specific locations (x,y) in the biological sample 804. A microfluidic probe is a non-contact, scanning platform that can hydrodynamically localize as little as 100 picoliters of a liquid cargo with micrometer precision.

By way of example only, the liquid cargo delivery device 802 dispenses a controlled amount of a processing solution (e.g., an aqueous solution) containing the vessels/molecular probes at multiple locations (i.e., $(x_1,y_1)$, $(x_1,y_2)$, $(x_1,y_3)$, etc.) in the biological sample 804. See step 812. As provided above, once the vessel/molecular probe is delivered to a specific location of the biological sample 804, the vessel delivers the molecular probes inside the cell(s) 806 at that specific location.

After the location-specific molecular probes have been delivered/inserted into the cells 806, the cells 806 are extracted from the biological sample 804. See step 814. However, even after being disassociated from the biological sample 804, the individual cells 806 retain the molecular probe with oligonucleotide sequence encoding the original position of the cells 806 in the biological sample 804. Thus, this positional data can be retained through the subsequent sequencing process. See step 816.

For example, one or more single cell sequencing techniques can be performed. Suitable single cell sequencing techniques include, but are not limited to, drop-seq, seq-well, cyto-seq, and combinations thereof. The single cell sequencing performed in step 816 can be used to identify the subject cell by the cell barcode (see above), the original position of the cells 806 within the biological sample 804 via the unique, location-specific oligonucleotide sequence of the molecular probes, and/or transcriptome information of the cells 806. Therefore, the combination of the present positional delivery and encoding process with extraction and single cell sequencing can collect concomitant spatial and molecular measurements (e.g., position coordinates and transcriptomes of one or more of the cells 806 in the biological sample 804) which, as described in conjunction with the description of step 110 of methodology 100 above, can be recorded and/or analyzed in silico.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 9:
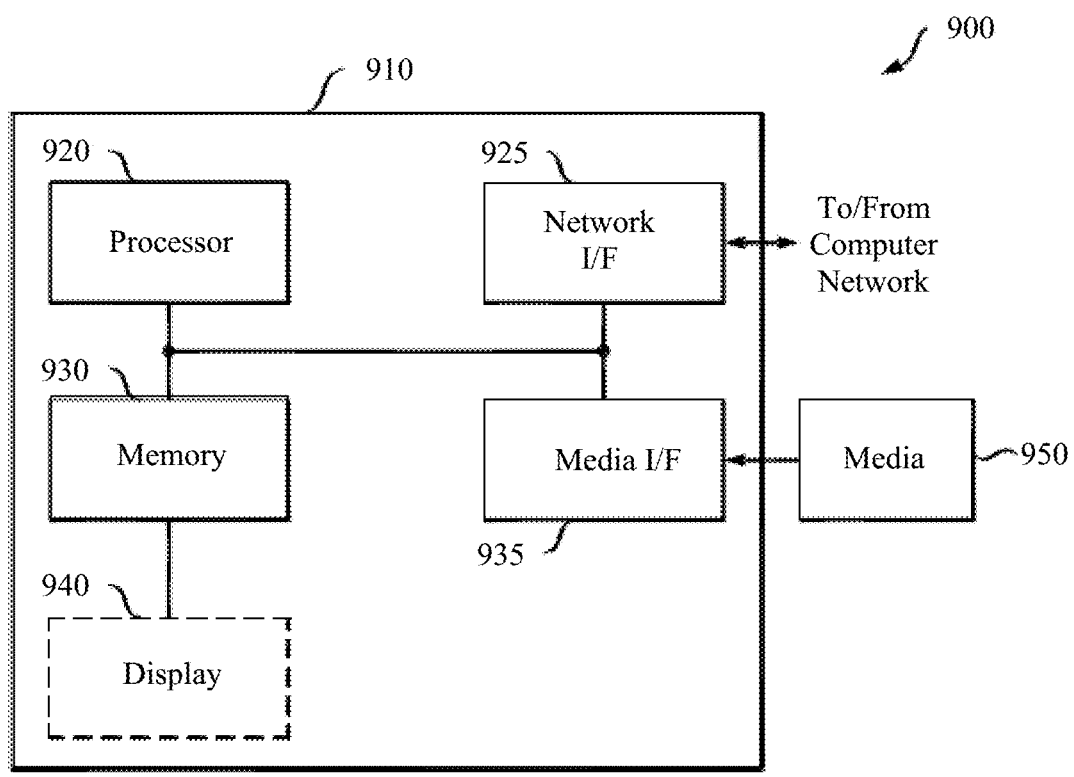
FIG. 9 is a diagram illustrating an exemplary apparatus for performing one or more of the methodologies presented herein according to an embodiment of the present invention.

Turning now to FIG. 9, a block diagram is shown of an apparatus 900 for implementing one or more of the methodologies presented herein. By way of example only, apparatus 900 can be configured to implement one or more of the steps of methodology 100 of FIG. 1. For instance, according to an exemplary embodiment, apparatus 900 may be configured to store and/or analyze the transcriptomic data extracted from the single cell sequencing along with the unique positional data obtained from the molecular probes indicating the original positioning of the cells in the biological sample.

Apparatus 900 includes a computer system 910 and removable media 950. Computer system 910 includes a processor device 920, a network interface 925, a memory 930, a media interface 935 and an optional display 940. Network interface 925 allows computer system 910 to connect to a network, while media interface 935 allows computer system 910 to interact with media, such as a hard drive or removable media 950.

Processor device 920 can be configured to implement the methods, steps, and functions disclosed herein. The memory 930 could be distributed or local and the processor device 920 could be distributed or singular. The memory 930 could be implemented as an electrical, magnetic or optical memory, or any combination of these or other types of storage devices. Moreover, the term "memory" should be construed broadly enough to encompass any information able to be read from, or written to, an address in the addressable space accessed by processor device 920. With this definition, information on a network, accessible through network interface 925, is still within memory 930 because the processor device 920 can retrieve the information from the network. It should be noted that each distributed processor that makes up processor device 920 generally contains its own addressable memory space. It should also be noted that some or all of computer system 910 can be incorporated into an application-specific or general-use integrated circuit.

Optional display 940 is any type of display suitable for interacting with a human user of apparatus 900. Generally, display 940 is a computer monitor or other similar display.

Figure 10:
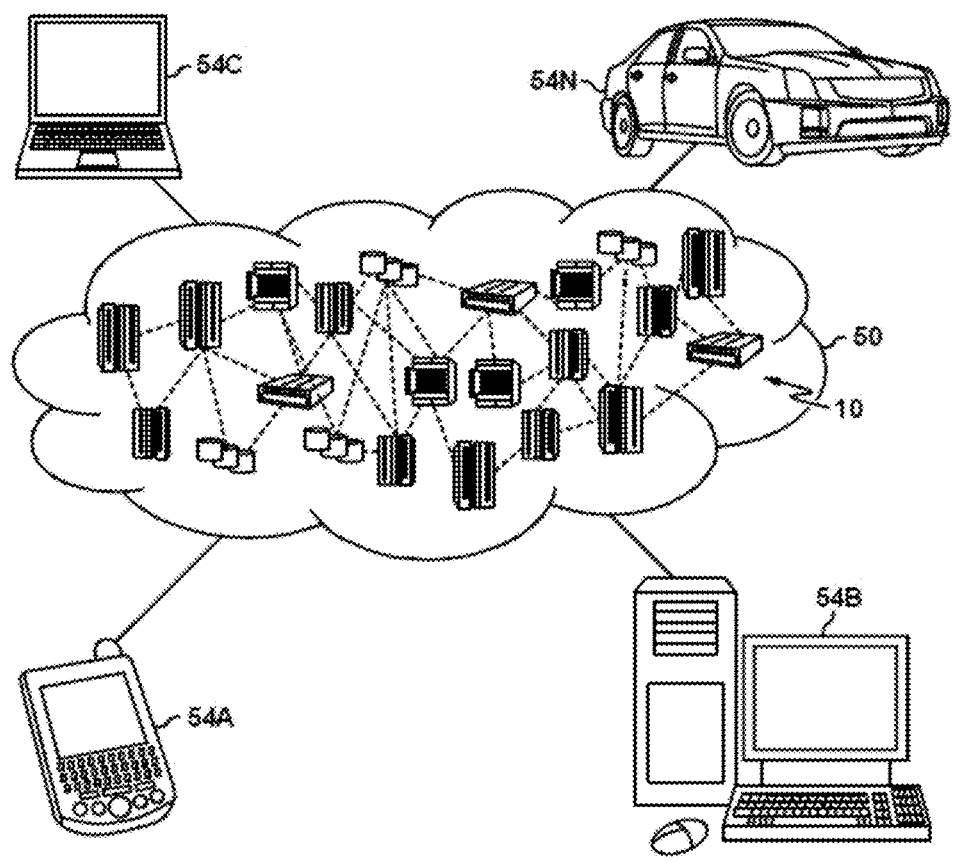
FIG. 10 depicts a cloud computing environment according to an embodiment of the present invention.
Figure 11:
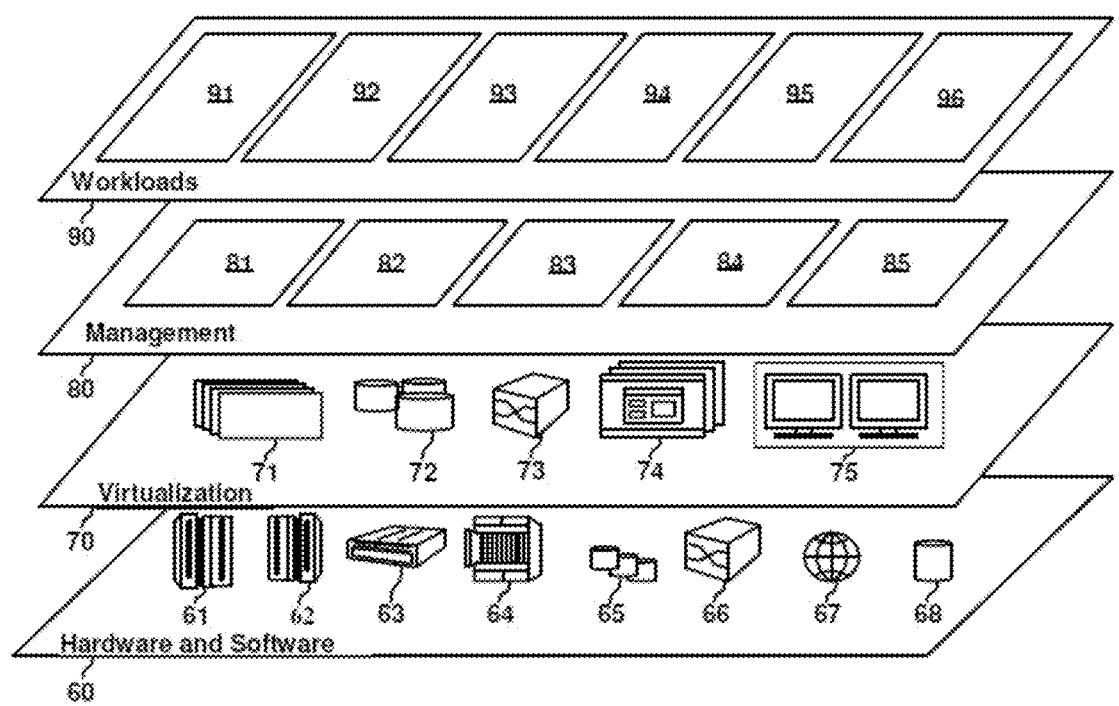
FIG. 11 depicts abstraction model layers according to an embodiment of the present invention.

Referring to FIG. 10 and FIG. 11, it is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 10, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 10 are intended to be illustrative only and that computing nodes 10 and cloud computing environment 50 can communicate with any type of computerized device over any type of network and/or network addressable connection (e.g., using a web browser).

Referring now to FIG. 11, a set of functional abstraction layers provided by cloud computing environment 50 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and cDNA library construction 96.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method, comprising:
    encoding cells in a biological sample for single cell sequencing by delivering molecular probes inside the cells that encode positional data comprising a position of the cells in the biological sample such that positional data is retained, via the molecular probes, even when the cells are disassociated from the biological sample for the single cell sequencing.

2. The method of claim 1, wherein the molecular probes comprise an oligonucleotide sequence that uniquely encodes the position of the cells in the biological sample.

3. The method of claim 2, wherein the molecular probes further comprise:
    a polymerase chain reaction (PCR) handle;
    a cell barcode; and
    a unique molecular identifier (UMI).

4. The method of claim 1, wherein the biological sample is selected from the group consisting of: a cell culture, a tissue sample, and combinations thereof.

5. The method of claim 1, further comprising:
    constructing a complementary deoxyribonucleic acid (cDNA) library of the molecular probes.

6. The method of claim 5, wherein the cDNA library is constructed using Moloney murine leukemia virus reverse transcriptase ("MMLV RT") technology.

7. The method of claim 1, wherein the molecular probes are delivered inside the cells using a vessel selected from the group consisting of: a retrovirus, cell-penetrating peptides, and bead microparticles.

8. The method of claim 7, wherein the vessel comprises a retrovirus, and wherein the retrovirus is a lentivirus.

9. The method of claim 7, wherein the vessel comprises cell-penetrating peptides, and wherein the cell-penetrating peptides comprise cleavable disulfide-linked cell-penetrating peptides.

10. The method of claim 7, wherein the vessel comprises bead microparticles, and wherein the bead microparticles comprise glass beads.

11. The method of claim 7, further comprising:
    linking the molecular probes to the vessel; and
    delivering the vessel with the molecular probes to specific locations of the biological sample where the vessel delivers the molecular probes inside the cells at the specific locations.

12. The method of claim 11, wherein the vessel with the molecular probes are delivered to the specific locations of the biological sample using a liquid cargo delivery device.

13. The method of claim 12, wherein the liquid cargo device comprises a microfluidic probe.

14. The method of claim 1, further comprising:
    extracting the cells containing the molecular probes from the biological sample; and
    performing single cell sequencing of the extracted cells.

15. A method, comprising:
    constructing a cDNA library of molecular probes that encode a position of cells in a biological sample;
    linking the molecular probes to a vessel;
    delivering the vessel with the molecular probes to specific locations of the biological sample where the vessel delivers the molecular probes inside the cells at the specific locations;
    extracting the cells containing the molecular probes from the biological sample, wherein the molecular probes retain positional data of the cells in the biological sample following the extracting; and
    performing single cell sequencing of the extracted cells.

16. The method of claim 15, wherein the molecular probes comprise an oligonucleotide sequence that uniquely encodes the position of the cells in the biological sample.

17. The method of claim 15, wherein the vessel is selected from the group consisting of: a retrovirus, cell-penetrating peptides, and bead microparticles.

18. The method of claim 15, wherein the vessel with the molecular probes are delivered to the specific locations of the biological sample using a liquid cargo delivery device.

19. The method of claim 18, wherein the liquid cargo device comprises a microfluidic probe.

* * * * *